US011266605B2

(12) United States Patent
Bravo Gonzaléz et al.

(10) Patent No.: US 11,266,605 B2
(45) Date of Patent: Mar. 8, 2022

(54) MODIFIED RELEASE COATED CAPSULES

(71) Applicant: Tillotts Pharma AG, Rheinfelden (CH)

(72) Inventors: Roberto Carlos Bravo Gonzaléz, Binningen (CH); Felipe José Oliveira Varum, Basel (CH); Thomas Buser, Nuglar (CH)

(73) Assignee: TILLOTTS PHARMA AG, Rheinfelden (CH)

( * ) Notice: Subject to any disclaimer, the term of this patent is extended or adjusted under 35 U.S.C. 154(b) by 0 days.

(21) Appl. No.: 15/312,571

(22) PCT Filed: May 13, 2015

(86) PCT No.: PCT/EP2015/060633
§ 371 (c)(1),
(2) Date: Nov. 18, 2016

(87) PCT Pub. No.: WO2015/177025
PCT Pub. Date: Nov. 26, 2015

(65) Prior Publication Data
US 2017/0119681 A1 May 4, 2017

(30) Foreign Application Priority Data
May 19, 2014 (EP) ..................... 14168892

(51) Int. Cl.
A61K 9/48 (2006.01)
(52) U.S. Cl.
CPC .......... *A61K 9/4891* (2013.01); *A61K 9/4808* (2013.01); *A61K 9/4825* (2013.01); *A61K 9/4833* (2013.01); *A61K 9/4866* (2013.01)
(58) Field of Classification Search
None
See application file for complete search history.

(56) References Cited

U.S. PATENT DOCUMENTS

| 5,330,759 A | * | 7/1994 | Pagay | .................. A61K 9/4891 |
| | | | | 424/452 |
| 5,930,984 A | * | 8/1999 | Furuya | .................... A61J 3/072 |
| | | | | 53/471 |
| 7,094,425 B2 | * | 8/2006 | Scott | .................... A61K 9/4891 |
| | | | | 424/451 |

FOREIGN PATENT DOCUMENTS

| EP | 2283830 A1 | * | 2/2011 | .......... A61K 9/4891 |
| WO | WO 2003/013480 A1 | | 2/2003 | |
| WO | WO 2004/030652 A2 | | 5/2004 | |
| WO | WO-2007122374 A2 | * | 11/2007 | .......... A61K 31/573 |
| WO | WO 2012/058695 A2 | | 5/2012 | |
| WO | WO 2013/054285 A1 | | 4/2013 | |
| WO | WO 2013/173811 A1 | | 11/2013 | |
| WO | WO 2014/152338 A1 | | 9/2014 | |

OTHER PUBLICATIONS

Jones, B.E. "Capsules, Hard" in Encyclopedia of Pharmaceutical Technology (2007) DOI: 10.1081 / E-EPT-120041346.*
Chang, R.K., et al. "Polymethacrylates" in Handbook of Pharmaceutical Excipients. Pharmaceutical Press and American Pharmacists Association 2009 (6th Edition) 525-533.*
Thoma, K., and K. Bechtold. Enteric coated hard gelatin capsules. CAPSUGEL Technical Bulletin (2000) pp. 1-17.*
Bowtie, W.J. "Liquid filling of hard gelatin capsules: a new technology for alternative formulations." Pharm. Technol. Eur 10 (1998): 84-90.*
Bauer, K.H., Uberzogene Arzneiformen. Wissenschaftliche Verlagsgesellschaft mbH, Stuttgart, 1988, p. 120. (Year: 1988).*
"Eudragit: Acrylic Polymers for Solid Oral Dosage Forms", Evonik Industries, Darmstadt, Germany, V. 2.3. (Aug. 2012).
"Eudragit: Setting Benchmarks in Oral Solid Dosage Forms Since 1954", Evonik Nutrition & Care GmbH, Darmstadt, Germany (Apr. 2011).
Kurt H. Bauer et al., *Überzogene Arzneiformen*, Wissenschaftliche Verlagsgesellschaf mbH, Stuttgart, 1988, (German original with English translation).

* cited by examiner

*Primary Examiner* — Bethany P Barham
*Assistant Examiner* — Peter Anthopolos
(74) *Attorney, Agent, or Firm* — Smith Patent, LLC; Chalin A. Smith

(57) ABSTRACT

The present invention relates to a modified release coated capsule and a process to obtain that capsule.

14 Claims, 16 Drawing Sheets

Example 1
Comparative Example 1A

Example 2
Comparative Example 2A

Example 3

Comparative Example 3

Example 3
Comparative Example 3

Comparative Example 4     Example 4

MODIFIED RELEASE COATED CAPSULES

PRIORITY

This application corresponds to the U.S. national phase of International Application No. PCT/EP2015/060633, filed May 13, 2015, which, in turn, claims priority to European Patent Application No. 14.168892.9 filed May 19, 2014, the contents of which are incorporated by reference herein in their entirety.

FIELD OF THE INVENTION

The present invention relates to a modified release coated capsule and a process to obtain that capsule.

BACKGROUND OF THE INVENTION

When orally administered, pharmaceutical preparations are generally disintegrated in the stomach. However, when a certain release profile of the pharmaceutical or nutritional ingredient is desired, oral pharmaceutical preparations can be coated with a so-called functional or modified release coating to achieve delayed or controlled release of an active pharmaceutical ingredient (API). Those coatings intended to protect the drug from the acidic environment of the gastric medium, to prevent the drug release in the stomach, or to provide release of an active ingredient to certain and specific section of the gastrointestinal tract (GIT) as e.g. the jejunum, duodenum, ileum, the colon and the rectum are commonly called delayed release coating formulations using enteric polymers.

In contrast to delayed drug release coatings, controlled release coatings are requested to control the release of the drug over a prolonged period of time. Depending on the drug release mechanism, controlled release approaches are also known in the pharmaceutical area as sustained, extended and prolonged release, respectively. Combinations of these coatings are possible as well.

Attempts have been made to provide drug-filled hard capsules with a modified release coating. During this development precoatings were found to be necessary because of imperfect adhesion of modified release coatings on hard gelatin capsules (K. S. Murthy et al., Pharm. Tech. 10, 36 (1986)). However, a precoating has the disadvantage of requiring more preparation steps resulting in more preparation time and material to be used, higher energy consumption and higher costs.

To overcome the disadvantages associated with a precoating, U.S. Pat. No. 4,670,287 discloses a method of film coating hard capsules under a vacuum. However, because of high technical efforts this technique has its limitations in industrial applicability.

In an alternative approach to overcome the disadvantages of precoatings enteric coated HPMC (hydroxypropyl methylcellulose) capsules were suggested to achieve intestinal targeting (E. T. Cole et al., Int. J. Pharm. 231 (2002) 83-95). Prior to the coating, the capsules were sealed with the LEMs (liquid encapsulation by microspray) process. Enteric coatings with an amount of enteric polymer of at least 6 mg/cm$^2$ showed no pores or cracks. However, E. T. Cole et al reported that due to the good compatibility between HPMC and the enteric films, variation in coating levels showed little influence on the dissolution profiles.

Furthermore, liquid filled capsules are frequently sealed either by using a band or using the LEMs technology to avoid leakage during further manufacturing steps, such as coating steps, packaging and so on. For powder or granules filled capsules, normally a band or other seal is not considered, even if a coating process is involved, as there is less risk of capsule opening. To avoid the additional sealing step, US 2011/0033530 suggests coating each capsule half before closing the capsule. It is said that as a result of coating the capsule halves prior to closing the capsule, in the closed state, the enteric coating of the lower part is partially overlapped by the upper part. The overlapped part of the coating is assumed having a sealing function which prevents the penetration of fluid through a possible gap between the lower part and the upper part. However, coating the two halves of a capsule shell prior to closing the capsule is a cumbersome process. Furthermore, there remains the risk that the coating may be damaged during capsule closure.

WO 2013/054285 discloses gastroretentive dosage systems wherein the extended-release layer comprises one or more extended-release polymer(s) and one or more coating additive(s). The system can be a band sealed capsule which is coated with an extended-release coating being applied until there is a weight gain of up to 15% w/w based on the total weight of the dosage form.

WO 2004/030652 discloses compositions having an inner core and at least two surrounding layers. The inner core may be a capsule which may be sealed via banding or LEMs. The inner layer may be a continuous coating having a coating weight of up to 25 mg/cm$^2$. The outer layer may be a wax at a coating weight of about 10 mg/cm$^2$.

WO 03/013480 discloses an enteric formulation of fluoxetine. The formulation may be in the form of a gelatin capsule comprising an optional smoothening coat, an enteric coating and an optional finishing coat. The enteric coating may comprise polymers in an amount of up to 20 mg/cm$^2$.

WO 2012/058695 discloses pharmaceutical compositions of (−)-17-(cyclobutylmethyl)morphinan-3,14-diol. The composition may be in the form of a capsule which optionally may be sealed by banding. Furthermore, the capsules may be coated with an aqueous composition of Eudragit® FS30D in an amount of up to 20 mg/cm$^2$.

Thus, there is still a need for modified release coated capsules not encountering the above problems. In particular, it would be desirable to provide modified release coated capsules which can be easily prepared at reduced costs using usual manufacturing processes. Furthermore, it would be desirable to provide a modified release coated capsule which can be prepared by the same method and with the same coating materials independent of the capsule shell material. Additionally, it would be desirable to provide a modified release coated capsule with a drug release profile which can be easily tailored according to the requirements.

SUMMARY OF THE INVENTION

It has now surprisingly been found that the above and other problems can be solved by applying a relatively thin modified release coating onto the capsule shell of a capsule comprising a band seal.

The present invention therefore relates to a capsule comprising a band seal and a modified release coating, characterized in that the modified release coating comprises a film forming agent in an amount of ≤8.0 mg/cm$^2$ of the modified release coating.

While applicants do not wish to be bound to any theory it is believed that the imperfect adhesion of enteric coatings on capsule shells might at least partly be associated to the gap between the body and the cap of the capsule. At this gap, mechanical stress might occur leading to possible cracks in the coating and reduced adhesion of the coating. However, it turned out that neither the prior art recommended subcoating nor sealing the gap by LEMs technology, nor the combination of both techniques, provided a satisfactory solution to the above problems. On the other hand, sealing the gap with a band surprisingly allowed to directly apply the enteric coating onto the capsule shell without any precoat between the capsule shell and the enteric coating. Furthermore, it was found that sealing the gap by a band allows the reduction of the amount of enteric polymer required for obtaining the same or even improved level of enteric coating compared to prior art coatings. This has the advantage that manufacturing costs are not only reduced by omitting the precoat, but can additionally be reduced by reducing the amount of enteric polymer. This reduction has the further advantage that the thickness of the enteric coating can be reduced thereby reducing the overall size and weight of the final capsule. Additionally, based on this invention resistance to release under simulated stomach conditions can be achieved already with very thin enteric coating films. In this context, the invention is of further advantage for tailoring drug release profile by adjusting the coating thickness according to the desired area of release within the gastrointestinal tract.

DETAILED DESCRIPTION OF THE PREFERRED EMBODIMENTS

Figure 1:
FIG. 1 shows capsules according to example 1 and according to comparative example 1A after immersion into acid solution.
Figure 1:

The capsule of the present invention in particular is for oral administration, such as for oral administration of a pharmaceutical or nutritional ingredient.

The size of the capsule is not particularly limited and can be any usual size, such as 000, 00, 0, 1, 2, 3, 4 or 5.

The capsule shell can be of any suitable material, such as gelatin, HPMC, pullulan or polyvinyl alcohol (PVA). HPMC and hard gelatin capsules are preferred. Hard gelatin capsules are particularly preferred.

Capsules and in particular hard capsules are usually prepared by closing a capsule body with a cap. According to the invention, the gap between the body and the cap of the capsule is sealed with a band. The band can be of any usual material being compatible with the material of the capsule shell. For example, the material of the band can be selected from gelatin, hydroxypropylmethyl cellulose, polyvinyl alcohol, polyvinyl alcohol copolymer or a mixture of two or more of these materials. Preferably, the band seal is of the same material as the capsule shell, such as a gelatin band, if hard-gelatin capsules are used. More preferably, the material of the band seal is gelatin or hydroxypropylmethyl cellulose.

The modified release coating of the capsule according to the invention may be a delayed release coating, such as an enteric coating, or a controlled release coating. Combinations of these coatings are also possible.

The function of the coating is usually attained by a film forming agent, in particular a film forming polymer. Any usual film forming agent known to the person skilled in the art for forming the desired coating may be used.

For an enteric coating the film forming agent usually comprises a compound which is insoluble in the gastrointestinal juice at a pH of below 5 and which is soluble in the intestinal juice at a pH at or above 5. Thus, this film forming agent dissolves in a pH dependent manner. The film forming agent has a pH threshold which is the pH below which it is insoluble and at or above which it is soluble. The pH of the surrounding medium triggers the dissolution of the film forming agent. Thus, none (or essentially none) of the film forming agent dissolves below the pH threshold. Once the pH of the surrounding medium reaches (or exceeds) the pH threshold, the film forming agent becomes soluble.

By "insoluble" it is understood that 1 g of the film forming agent requires more than 10,000 ml of solvent (surrounding medium) to dissolve at a given pH. By "soluble", it is understood that 1 g of the film forming agent requires less than 10,000 ml, preferably less than 5,000 ml, more preferably less than 1,000 ml, even more preferably less than 100 ml or 10 ml of solvent to dissolve at a given pH. "Surrounding medium" means the medium in the gastrointestinal tract, such as the gastric juice or intestinal juice. Alternatively, the surrounding medium may be an in vitro equivalent of the medium in the gastrointestinal tract.

The normal pH of gastric juice is usually in the range of 1 to 3. The film forming agent for intestinal, such as colon targeting should thus be insoluble below pH 5 and should be soluble at or above pH 5. The film forming agent therefore is usually insoluble in gastric juice. Such material may be referred to as an "enteric" material. The pH of intestinal juice gradually increases to about 7 to 8 along the small intestine. A film forming agent for intestinal targeting therefore becomes soluble in the terminal ileum/colon and allows release of e.g. the active agent from the capsule. The film forming agent preferably has a pH threshold of 6.5, more preferably of 7.

Examples of suitable film forming agents for intestinal targeting and in particular for the preparation of the coating surrounding the capsule are acrylate polymers, cellulose polymers and polyvinyl-based polymers, or other polymers. Examples of suitable cellulose polymers include cellulose acetate phthalate, cellulose acetate trimellitate, cellulose acetate succinate, hydroxypropylmethyl cellulose phthalate, hydroxypropylmethyl cellulose acetate succinate and carboxymethylethyl cellulose acetate butyrate. Examples of suitable polyvinyl-based polymers include polyvinyl acetate phthalate.

In a preferred embodiment the material for intestinal targeting is a co-polymer of a (meth)acrylic acid and a (meth)acrylic acid $C_{1-4}$ alkyl ester, for instance, a co-polymer of methacrylic acid and methacrylic acid methyl ester. Suitable examples of such co-polymers are usually anionic. Furthermore, these co-polymers usually are not sustained release polymethacrylates. The ratio of carboxylic acid groups to methylester groups in these co-polymers determines the pH at which the copolymer is soluble. The acid:ester ratio may be from about 2:1 to about 1:3, e.g. about 1:1 or, about 1:2. The molecular weight of such anionic co-polymers is usually from about 120,000 to 150,000, preferably about 135,000.

Known anionic poly(methacrylic acid/methyl methacrylate) co-polymers include Eudragit® L (pH threshold about 6.0), Eudragit® S (pH threshold about 7) and Eudragit® FS (pH threshold about 7). Eudragit® L 100-55 which is a copolymer of methacrylic acid and ethylacetate and which has a pH threshold of about 5.5 is also suitable. The Eudragit® copolymers can be obtained from Evonik.

In addition or alternatively to the above described compounds having a pH threshold the film forming agent for intestinal, such as colon targeting may comprise a compound which is susceptible to attack by colonic bacteria, such as polysaccharides. Suitable polysaccharides are for example starch, amylose, amylopectine, chitosan, chondroitine sulfate, cyclodextrine, dextrane, pullulan, carrageenan, scleroglucan, chitin, curdulan, pectin, guar gum, xanthan gum and levan.

Alternatively or additionally, the modified release coating can be a controlled release coating. These coatings are able to provide release of the active substance after a predetermined time after administration or a controlled release over time.

Galenical principles used to achieve the different release forms typically reduce the dissolution of the active ingredient; establish diffusion barriers including osmotic systems and erosion systems. With regards to functional coatings the focus is on establishment of diffusion barriers. Diffusion barriers can be established by membranes controlling the diffusion being permeable or not; by using a controlling principle as pH or natural degradation during the GIT transit; by using a controlled release matrix releasing an active ingredient contained in the matrix controlled by diffusion; by using a membrane controlled osmotic effect, or by using a diffusion membrane eroding after degradation.

Suitable polymers for diffusion membranes that typically are gastric resistant are cellulose derivatives as cellulose acetate phthalate (CAP), Hydroxypropyl methylcellulose phthalate (HPMCP), polymethacrylates and polyvinylacetate phthalate.

In one embodiment of the present invention, the film forming agent does not comprise cellulose acetate. In another embodiment of the present invention, the film forming agent does not comprise cellulose acetate phthalate.

In one embodiment of the present invention, the film forming agent does not comprise hydroxypropylmethyl cellulose phthalate.

Suitable polymers for a controlled release matrix coating are digestible, long chain (C8-C50, especially C12-C40), substituted or unsubstituted hydrocarbons, such as fatty acids, fatty alcohols, glyceryl esters of fatty acids, mineral and vegetable oils and waxes, polyalkylene glycols, hydrophilic polymers, such as gums, cellulose ethers, acrylic resins and protein derived materials, and in general polymers that are insoluble over the entire pH-range, and combinations thereof.

Further suitable polymers are carboxy methylethylcellulose (CMEC) or ethylcellulose which provide a release by diffusion but are not entirely gastric resistant. Further examples include polymethacrylate sustained release polymers, such as Eudragit® RS, RL, NM and NE.

In one embodiment of the present invention, the film forming agent does not comprise ethylcellulose.

In one embodiment of the present invention, the film forming agent does not comprise Eudragit® RL PO. In another embodiment of the present invention, the film forming agent does not comprise Eudragit® FS, such as Eudragit® FS30D.

Suitable polymers for an erosion system among others are cellulose ether derivatives and degradable natural polymers as polysaccharides.

With the materials mentioned above a person skilled in the art is able to tailor the composition of the coatings in a way that the release of the active ingredient starts, or takes place, specifically at the targeted site of the GIT. This can, among others, be achieved by the means of introducing pores to make the membrane permeable, or more permeable, by including pore formers and/or further excipients; by introducing further excipients for erosion as e.g. using degradable natural polymers as polysaccharides or synthetic polymers that dissolve at a certain pH.

Mixtures of two or more film forming agents may be used as appropriate.

Optionally, the modified release coating may additionally comprise conventional excipients, such as plasticizers for film formation (for example triethylcitrate), anti-tacking agents (such as glyceryl monostearate), colorants, pigments, solublilizers, dispersion agents and surfactants. For example such excipients may be included in amounts known to the skilled person of e.g. up to 30% by weight of the total weight of the coating.

A particular advantage of the present invention is that the amount of film forming agent can be lower than usual. In fact, it was found that a modified release coating comprising a low amount of film forming agent being applied onto the capsule shell (with a band seal) with or without any precoat shows improved adhesion and can even impart improved dissolution properties to the capsule compared to a modified release coating comprising a higher amount of film forming agent. It was surprisingly found that this beneficial effect does not occur if the capsule is sealed using an alternative method, namely the LEMs technology.

As demonstrated by the present comparative examples either sealing the capsules by LEMs technology alone or in combination with a precoat does not provide satisfactory acid resistance to the capsules even if a high amount of enteric coating is applied.

Consequently, the present invention does not only save material and, thus, costs, but constitutes a surprising beneficial technical effect over prior art coated capsules. Thus, the film forming agent according to the invention is present in an amount of ≤8.0 mg, preferably from about 1 mg to ≤8.0 mg, such as from about 3.0 mg to ≤8.0 mg, more preferably of from >3.0 mg to ≤8.0 mg, such as from about 3.1 mg to ≤8.0 mg, from about 3.2 mg to ≤8.0 mg, from about 3.3 mg to ≤8.0 mg, from about 3.4 mg to ≤8.0 mg or from about 3.5 mg to ≤8.0 mg. In another embodiment, the amount of the film forming agent is from about 2 mg to about 7 mg, more preferably of from >2.0 mg to about 7.0 mg, such as from about 2.1 mg to about 7.0 mg, from about 2.2 mg to about 7.0 mg, from about 2.3 mg to about 7.0 mg, from about 2.4 mg to about 7.0 mg, from about 2.5 mg to about 7.0 mg, from about 3.0 mg to about 7.0 mg, from about 3.1 mg to about 7.0 mg, from about 3.2 mg to about 7.0 mg, from about 3.3 mg to about 7.0 mg, from about 3.4 mg to about 7.0 mg, from about 3.5 mg to about 7.0 mg. Even more preferred examples are of from about 2.0 mg to about 6.0 mg, from about 3.0 mg to about 6.0 mg and from about 3.5 mg to about 6.0 mg and most preferably at about 4 mg, each of the above as amount per $cm^2$ of the modified release coating.

In one embodiment of the present invention, the film forming agent according to the invention is present in an amount of about 1 mg, about 2 mg, about 3 mg, about 4 mg, about 5 mg, about 6 mg, about 7 mg, or about 8 mg, each amount per $cm^2$ of the modified release coating.

In another embodiment of the present invention, the film forming agent according to the invention is not present in an amount of 3 mg per $cm^2$ of the modified release coating.

In one embodiment, the capsule according to the present invention is filled with one or more pharmaceutically active ingredients. In a preferred embodiment, the one or more pharmaceutically active ingredients are selected from compounds used for the treatment of inflammatory bowel disease, such as mesalazine, prednisone, methotrexate and antibiotics, such as metronidazole. Particularly preferred is mesalazine.

The capsule according to the invention may comprise one or more additional coatings, preferably above the modified release coating. In this context, "above" means that the additional coating may be coated on the modified release coating. The additional coating may also be between the capsule shell and the coating, although it is preferred that there is no coating and in particular no precoat between the capsule shell and the modified release coating. The additional coating may for example be present for increasing the stability of the capsule against humidity or for increasing the visual appearance of the capsule.

Any of the above coatings including the modified release coating may comprise one or more pharmaceutically active ingredients. Any coating additional to the modified release coating may consist of the one or more pharmaceutically active ingredients.

In one embodiment, the one or more pharmaceutically active ingredients in the above coatings have a combined effect together with the pharmaceutically active ingredient within the capsule.

In one embodiment, the capsule according to the present invention is filled with one or more pharmaceutically active ingredients and the additional coating above the modified release coating comprises or consists of one or more pharmaceutically active ingredients. The one or more pharmaceutically active ingredients within the capsule and within the additional coating can be the same or different. In a preferred embodiment the one or more pharmaceutically active ingredients within the capsule and within the coating are different.

In one embodiment, the capsule according to the present invention is filled with one or more pharmaceutically active ingredients and the modified release coating comprises one or more pharmaceutically active ingredients. The one or more pharmaceutically active ingredients within the capsule and within the modified release coating can be the same or different. In a preferred embodiment the one or more pharmaceutically active ingredients within the capsule and within the modified release coating are different.

In one embodiment, the capsule according to the present invention is filled with mesalazine (5-ASA) and the additional coating above the modified release coating comprises metronidazole, or an ester or salt thereof, in particular metronidazole benzoate.

In another embodiment, the capsule according to the present invention is filled with mesalazine (5-ASA) and the coating comprises metronidazole, or an ester or salt thereof, in particular metronidazole benzoate.

In one embodiment, the capsule according to the present invention does not comprise an additional coating, in particular any additional coating above the modified release coating.

In another embodiment, the capsule according to the present invention does not comprise an additional coating (in particular above the modified release coating) comprising carnuba wax or paraffin wax, in particular waxes.

In a further embodiment, the capsule according to the present invention does not comprise a coating, such as an additional coating, comprising one or more pharmaceutically active ingredients.

The capsule according to the invention may be filled with a liquid, semi-solid and/or solid material, such as a solution, dispersion, paste, gel, wax, powder or granules. The material may comprise a nutritional ingredient and/or an active pharmaceutical ingredient either alone or in combination with usual excipients. Capsules filled with liquid or semi-solid material are particularly preferred. Most preferred are capsules filled with liquid material.

In one embodiment, the capsule according to the present invention is filled with a powder and the film forming agent is present in an amount of from >3.0 mg to ≤8.0 mg, such as from about 3.1 mg to ≤8.0 mg, from about 3.2 mg to ≤8.0 mg, from about 3.3 mg to ≤8.0 mg, from about 3.4 mg to ≤8.0 mg or from about 3.5 mg to ≤8.0 mg, and more preferably at about 4 mg, each amount per $cm^2$ of the modified release coating.

In another embodiment, the capsule according to the present invention is filled with a powder and the film forming agent is present in an amount of from >2.0 mg to ≤8.0 mg, such as from about 2.1 mg to ≤8.0 mg, from about 2.2 mg to ≤8.0 mg, from about 2.3 mg to ≤8.0 mg, from about 2.4 mg to ≤8.0 mg or from about 2.5 mg to ≤8.0 mg, each amount per $cm^2$ of the modified release coating.

In yet a further embodiment, the capsule according to the present invention is filled with a powder or granules and the film forming agent is present in an amount of from >2.0 mg to about 7.0 mg, such as from about 2.1 mg to about 7.0 mg, from about 2.2 mg to about 7.0 mg, from about 2.3 mg to about 7.0 mg, from about 2.4 mg to about 7.0 mg, from about 2.5 g to about 7.0 mg, from about 3.0 mg to about 7.0 mg, from about 3.1 mg to about 7.0 mg, from about 3.2 mg to about 7.0 mg, from about 3.3 mg to about 7.0 mg, from about 3.4 mg to about 7.0 mg, or from about 3.5 mg to about 7.0 mg, such as from >2.0 mg to about 6.0 mg, from about 3.0 mg to about 6.0 mg and from 3.5 mg to about 6.0 mg, each amount per cm² of the modified release coating.

In one embodiment, the capsule according to the present invention is not filled with a powder.

In one embodiment, the capsule according to the present invention is filled with pluralities of particles, such as pellets, minitablets, granules, etc.

In one embodiment, the capsule according to the present invention is filled with an above described plurality of particles and the film forming agent is present in an amount of from >3 mg to ≤8.0 mg, such as from about 3.1 mg to ≤8.0 mg, from about 3.2 mg to ≤8.0 mg, from about 3.3 mg to ≤8.0 mg, from about 3.4 mg to ≤8.0 mg or from about 3.5 mg to ≤8.0 mg, and more preferably at about 4 mg, each amount per cm² of the modified release coating.

In another embodiment, the capsule according to the present invention is filled with an above described plurality of particles and the film forming agent is present in an amount of from >2 mg to ≤8.0 mg, such as from about 2.1 mg to ≤8.0 mg, from about 2.2 mg to ≤8.0 mg, from about 2.3 mg to ≤8.0 mg, from about 2.4 mg to ≤8.0 mg or from about 2.5 mg to ≤8.0 mg, each amount per cm² of the modified release coating.

In yet a further embodiment, the capsule according to the present invention is filled with an above described plurality of particles and a film forming agent is present in an amount of from >2.0 mg to about 7.0 mg, such as from about 2.1 mg to about 7.0 mg, from about 2.2 mg to about 7.0 mg, from about 2.3 mg to about 7.0 mg, from about 2.4 mg to about 7.0 mg, from about 2.5 g to about 7.0 mg, from about 3.0 mg to about 7.0 mg, from about 3.1 mg to about 7.0 mg, from about 3.2 mg to about 7.0 mg, from about 3.3 mg to about 7.0 mg, from about 3.4 mg to about 7.0 mg, or from about 3.5 mg to about 7.0 mg, such as from >2.0 mg to about 6.0 mg, from about 3.0 mg to about 6.0 mg and from 3.5 mg to about 6.0 mg, each amount per cm² of the modified release coating.

In one embodiment, the capsule according to the present invention is not filled with an above described plurality of particles. In a preferred embodiment, the capsule according to the present invention is not filled with minitablets or pellets.

In one embodiment, the capsule according to the present invention is filled with a liquid and the film forming agent is present in an amount of from >3 mg to ≤8.0 mg, such as from about 3.1 mg to ≤8.0 mg, from about 3.2 mg to ≤8.0 mg, from about 3.3 mg to ≤8.0 mg, from about 3.4 mg to ≤8.0 mg or from about 3.5 mg to ≤8.0 mg, and more preferably at about 4 mg, each amount per cm² of the modified release coating.

In another embodiment, the capsule according to the present invention is filled with a liquid and the film forming agent is present in an amount of from >2 mg to ≤8.0 mg, such as from about 2.1 mg to ≤8.0 mg, from about 2.2 mg to ≤8.0 mg, from about 2.3 mg to ≤8.0 mg, from about 2.4 mg to ≤8.0 mg or from about 2.5 mg to ≤8.0 mg, each amount per cm² of the modified release coating.

In yet a further embodiment, the capsule according to the present invention is filled with a liquid and the film forming agent is present in an amount of from >2.0 mg to about 7.0 mg, such as from about 2.1 mg to about 7.0 mg, from about 2.2 mg to about 7.0 mg, from about 2.3 mg to about 7.0 mg, from about 2.4 mg to about 7.0 mg, from about 2.5 g to about 7.0 mg, from about 3.0 mg to about 7.0 mg, from about 3.1 mg to about 7.0 mg, from about 3.2 mg to about 7.0 mg, from about 3.3 mg to about 7.0 mg, from about 3.4 mg to about 7.0 mg, or from about 3.5 mg to about 7.0 mg, such as from >2.0 mg to about 6.0 mg, from about 3.0 mg to about 6.0 mg and from 3.5 mg to about 6.0 mg, each amount per cm² of the modified release coating.

The present invention further relates to a process to obtain the above described capsule comprising the steps of optionally filling the capsule body with a liquid, semi-solid and/or solid material, closing the capsule with a cap, sealing the gap between body and cap with a band and applying a modified release coating onto the capsule shell such that the modified release coating comprises a film forming agent in an amount of 8.0 mg/cm² of the modified release coating.

Coating can be carried out by any usual method known to the person skilled in the art. For example, a film comprising the film forming agent and optional excipients can be applied as an organic solution, as an aqueous-organic coating emulsion, as an aqueous-organic coating solution, as an aqueous dispersion or as a neutralized aqueous solution. As organic liquids, alcohols and in particular ethanol may be used.

For example, the solution, emulsion or dispersion of the film forming agent and optionally excipients may be sprayed onto the capsule in an amount required for providing the desired amount of dry film forming agent per cm² of the final modified release coating.

The invention will now be further illustrated by the following examples which are not intended to be construed as being limiting.

Example 1

Size 1 hard gelatin capsules were filled with a model powder formulation containing methylene blue as marker. The capsules were closed and sealed with a gelatin band. Without any precoat, the capsules were then coated with aqueous Eudragit L30D-55 in amounts of 4 mg/cm² and 6 mg/cm², respectively, each relating to the dry amount of film forming agent per cm² of the final coating.

Comparative Example 1A

Capsules were manufactured in the same manner as in example 1 but without sealing the capsules with the gelatin band prior to the enteric coating.

Comparative Example 1B

Capsules were manufactured in the same manner as in comparative example 1A but with 3 mg/cm² HPMC precoat between the gelatin capsule shell and the Eudragit L30D-55 enteric coating.

Evaluation of Capsules According to Example 1 and Comparative Examples 1A and 1B The acid resistance of the capsules obtained in example 1 and comparative examples 1A and 1B was tested by immersing the capsules for 120 minutes in 0.1 N HCl solution. After the capsules were recovered from the solution, they were visually controlled. Due to the use of methylene blue as marker in the model powder formulation filled into the capsules even small leakages could be easily observed.

Figure 2:
FIG. 2 shows capsules according to comparative example 1B after immersion into acid solution.

The results of this test are shown in FIGS. 1 and 2. FIG. 1 shows the capsules of example 1 being coated with 4 mg/cm² of the film forming agent after recovering from the acid solution. No deterioration of the capsules or leakage was observed.

In contrast thereto, the capsules of comparative example 1A showed strong deterioration and leakage (capsules turned blue) after immersion in the acid solution although they were coated with three-times the amount of enteric coating compared to example 1, namely 12 mg/cm² of film forming agent. This comparative example demonstrates that sealing the capsules with a band allows the use of much lower amounts of enteric coating material for obtaining capsules having even improved properties.

The capsules of comparative example 1B after immersion into the acid solution are shown in FIG. 2. These capsules were prepared according to usual prior art methods using a HPMC precoat and being enterically coated with 6 mg/cm² of the film forming agent. Despite the precoat the capsules showed strong deterioration. Furthermore, the capsules turned blue indicating that the marker substance leaked out of the capsules. Again, the banded capsules without any precoat according to the invention (example 1) exhibit an improved acid resistance although they are coated with a lower amount of enteric coating.

Furthermore, the release profiles of the capsules were measured using pH 6.8 Hanks buffer. In vitro dissolution studies were performed on a USP type II apparatus using a paddle speed of 50 rpm and a media temperature of 37±0.5° C. Capsules were first tested in 900 ml 0.1 N HCl for 2 hours followed by 8 or 10 hours in Hanks buffer (pH 6.8). The pH of the buffer was stabilized at 6.8±0.05 by continuously sparging with 5% $CO_2$/95% $O_2$. Methylene blue absorbance measurements were taken at 5 minute intervals, with an absorbance wavelength of 663 nm. The composition per litre of Hanks buffer was 0.06 g of $KH_2PO_4$, 0.06 g $Na_2HPO_4.2H_2O$, 8.0 g NaCl, 0.4 g KCl, 0.2 g $MgSO_4.7H_2O$, 0.139 g $CaCl_2.2H_2O$ and 0.350 g $NaHCO_3$.

Figure 3:
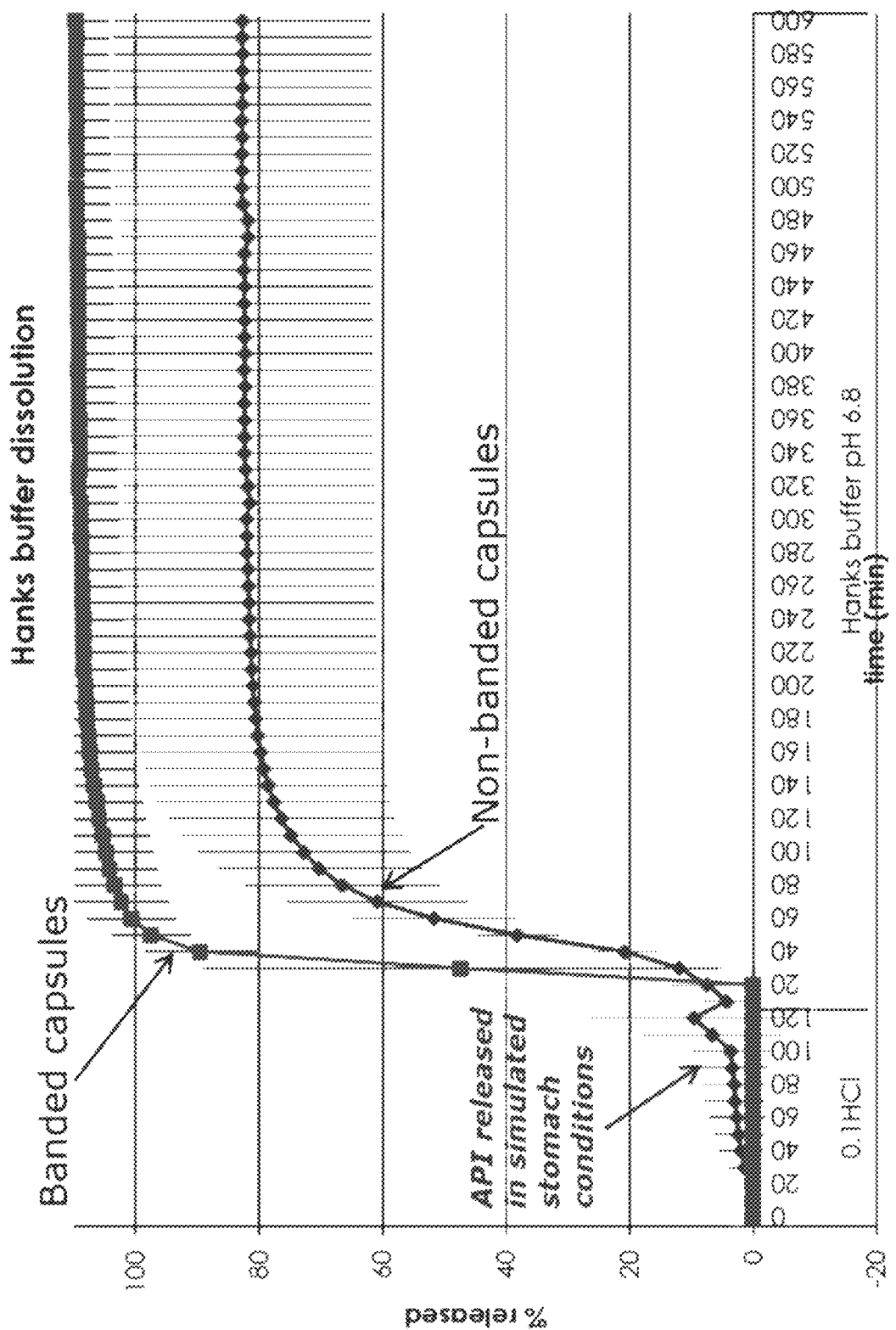
FIG. 3 shows the release profiles of the capsules according to example 1 and according to comparative example 1A.

The release profiles of the capsules according to example 1 (banded capsules) and of the capsules of comparative example 1A (non-banded capsules) are shown in FIG. 3. Both capsules were coated with 4 mg/cm² of the film forming agent. As expected from the above acid resistance test, release of the model active pharmaceutical ingredient (API) from the non-banded capsules according to comparative example 1A started already under the simulated stomach conditions in the 0.1 N HCl solution. Furthermore, the non-banded capsules did not release all of the API even after prolonged time in Hanks buffer. In contrast thereto, the capsules according to the invention (banded; example 1) did not release any of the API under the simulated stomach conditions but released their complete API content after a lag time of about 20 minutes in the bicarbonate buffer.

Figure 4:
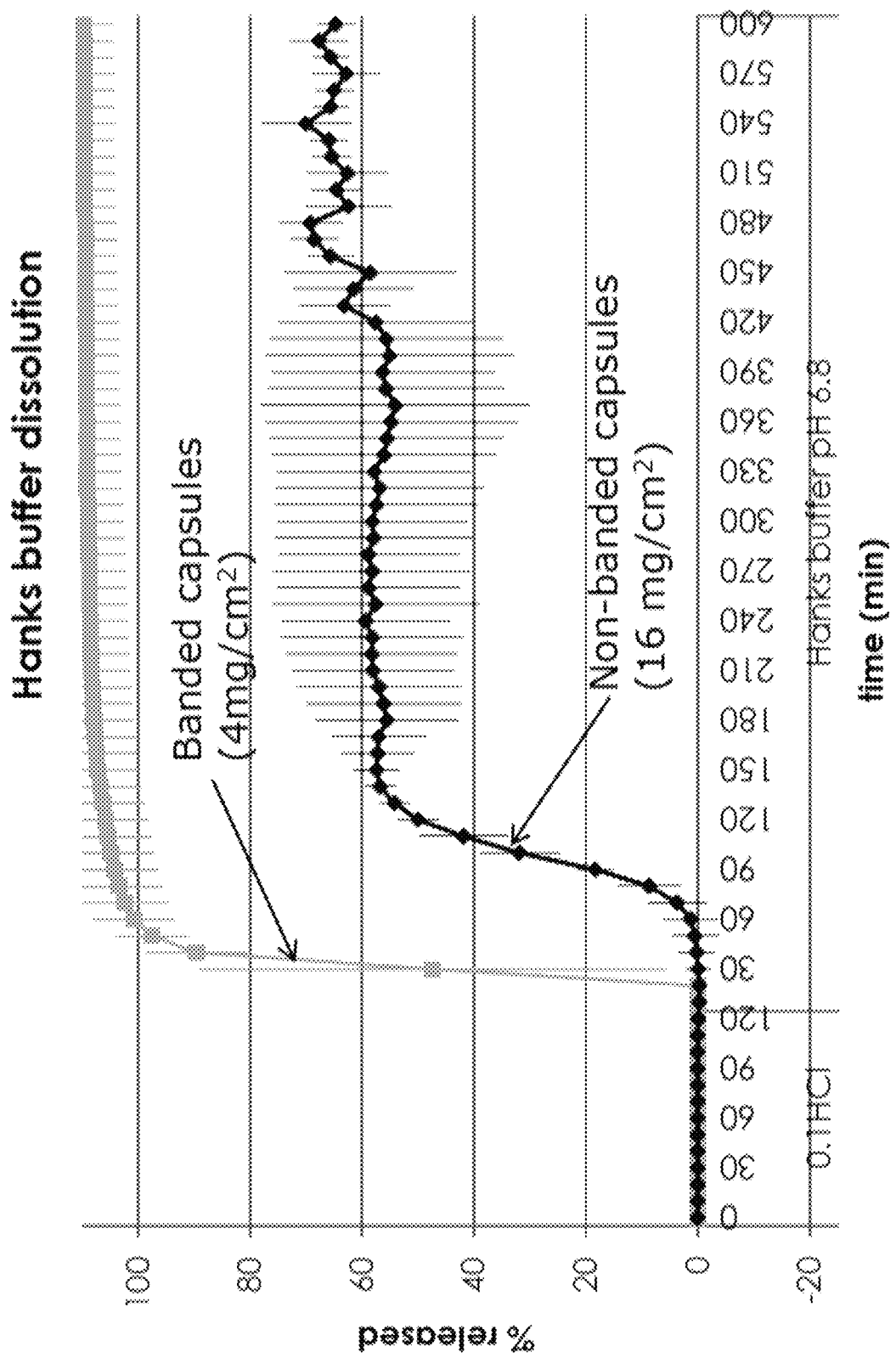
FIG. 4 shows the release profiles of the capsules according to example 1 and according to comparative example 1A (with a higher amount of coating).

FIG. 4 shows a comparison of the release profiles of banded capsules according to example 1 coated with 4 mg/cm² of the film forming agent and non-banded capsules according to example 1A being coated with as much as 16 mg/cm² of the film forming agent. While the significant increase in the amount of enteric coating suppressed the premature release of the API under simulated stomach conditions, the API was released at a later lag time, which could results in a too late release in vivo leading to lower oral bioavailability of drugs preferably absorbed in the proximal small intestine. Only up to about 60% of API was released even after prolonged time in the bicarbonate buffer solution.

Example 2

Capsules were prepared in the same manner as in example 1 but using organic Eudragit L100-55 for preparing the enteric coating.

Comparative Example 2A

Capsules were prepared in the same manner as in example 2 but without sealing the capsules with the gelatin band prior to the enteric coating.

Comparative Example 2B

Figure 5:
FIG. 5 shows capsules according to example 2 and capsules according to comparative example 2A after immersion into acid solution.
Figure 5:
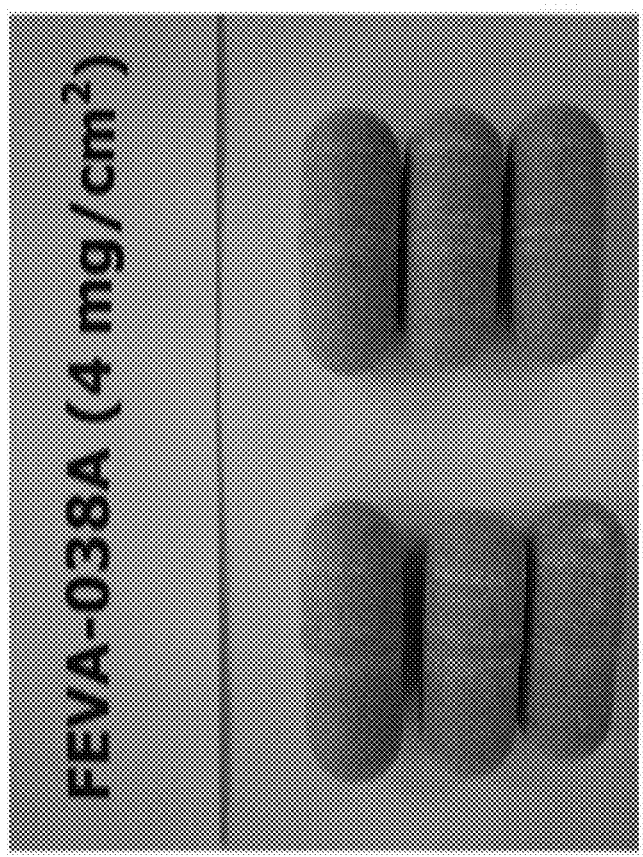
Figure 6:
FIG. 6 shows capsules according to comparative example 2B after immersion into acid solution.
Figure 7:
FIG. 7 shows capsules according to example 3 and capsules according to comparative example 3 after immersion into acid solution.
Figure 7:
Figure 8:
FIG. 8 shows capsules according to example 3 and capsules according to comparative example 3 after immersion into acid solution.
Figure 8:
Figure 9:
FIG. 9 shows capsules according to comparative example 3 after immersion into acid solution.

Capsules were prepared in the same manner as in comparative example 2A but using a precoat of 3 mg/cm² of HPMC prior to the enteric coating.
Evaluation of Capsules According to Example 2 and Comparative Examples 2A and 2B
The acid resistance of the capsules obtained in example 2 and comparative examples 2A and 2B were tested as described above with respect to the capsules of example 1 and comparative examples 1A and 1B. The results are shown in FIGS. 5 and 6 for the capsules obtained in example 2 being coated with 4 mg/cm² of the film forming agent (FIG. 5), the capsules obtained in comparative example 2A being coated with 16 mg/cm² of the film forming agent (FIG. 5) and the capsules obtained in comparative example 2B being coated with a precoat and with 4 mg/cm² of the film forming agent (FIG. 6).

As can be seen, the capsules according to the invention (example 2) exhibited no deterioration or leakage while the capsules being coated with even four times the amount of enteric coating obtained in comparative example 2A and the capsules being coated with the same amount of enteric coating as the capsules of example 2 but additionally comprising a precoat obtained in comparative example 2B exhibited strong deterioration and leakage.

Example 3

Capsules were manufactured in the same manner as in example 1 but being filled with a model liquid formulation containing methylene blue as marker.

Comparative Example 3

Capsules were prepared in the same manner as in example 3 but being sealed with the LEMs technology instead of the sealing band.

Example 4

Capsules were prepared in the same manner as in example 3 but being precoated with 3 mg/cm² of HPMC prior to the coating with the enteric coating.

Comparative Example 4

Capsules were prepared in the same manner as in comparative example 3 but being precoated with 3 mg/cm² of HPMC prior to the coating with the enteric coating.
Evaluation of Capsules According to Examples 3 and 4 and Comparative Examples 3 and 4
The acid resistance of the capsules obtained in example 3 and 4 and comparative examples 3 and 4 was tested as described above for the capsules of example 1 and comparative examples 1A and 1B. The results are shown in FIGS. 7 to 10. While the capsules according to the invention (example 3) being coated with 4 mg/cm² (FIG. 7) and 6 mg/cm² (FIG. 8) of the film forming agent exhibited no deterioration or leakage (the red color of the capsules remained unchanged), the capsules of comparative example 3 being sealed with the LEMs technology instead of the sealing band and being coated with the same amount (4 mg/cm$^2$) (FIG. 7), 6 mg/cm$^2$ (FIG. 8), 10 mg/cm$^2$ (FIG. 9) and even 16 mg/cm$^2$ (FIG. 9) of the film forming agent showed strong leakage of the blue marker agent (as observed by the blue color of the capsules after immersion).

Figure 10:
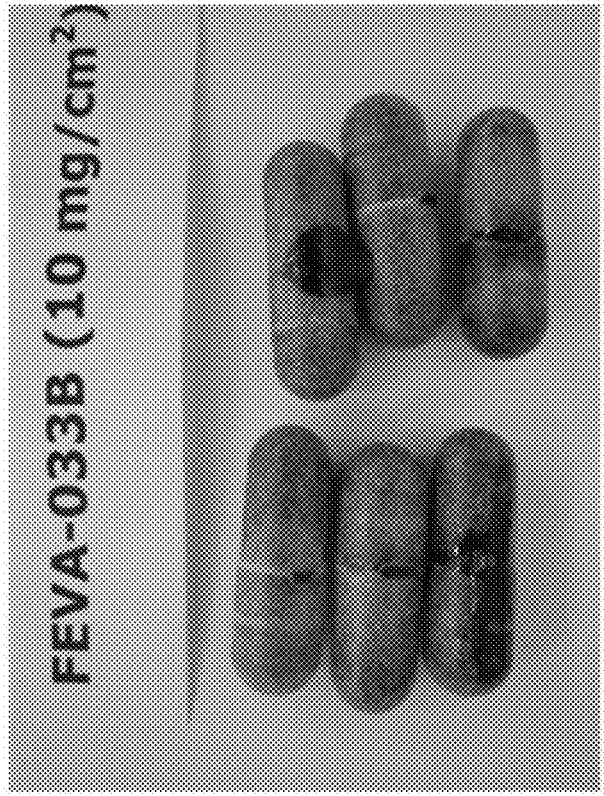
FIG. 10 shows capsules according to example 4 and capsules according comparative example 4 after immersion into acid solution.
Figure 10:

Furthermore, the capsules according to the invention (example 4) being coated with 3 mg/cm$^2$ HPMC precoat and 4 mg/cm$^2$ enteric coating exhibited no deterioration or leakage (FIG. 10; capsules remained red). However, the capsules of comparative example 4 being sealed with the LEMs technology instead of the sealing band and being coated with as much as 10 mg/cm$^2$ of the enteric film forming agent and additionally comprising the precoat also showed leakage of the marker agent (as observed by the blue color of the capsules after immersion).

Figure 11:
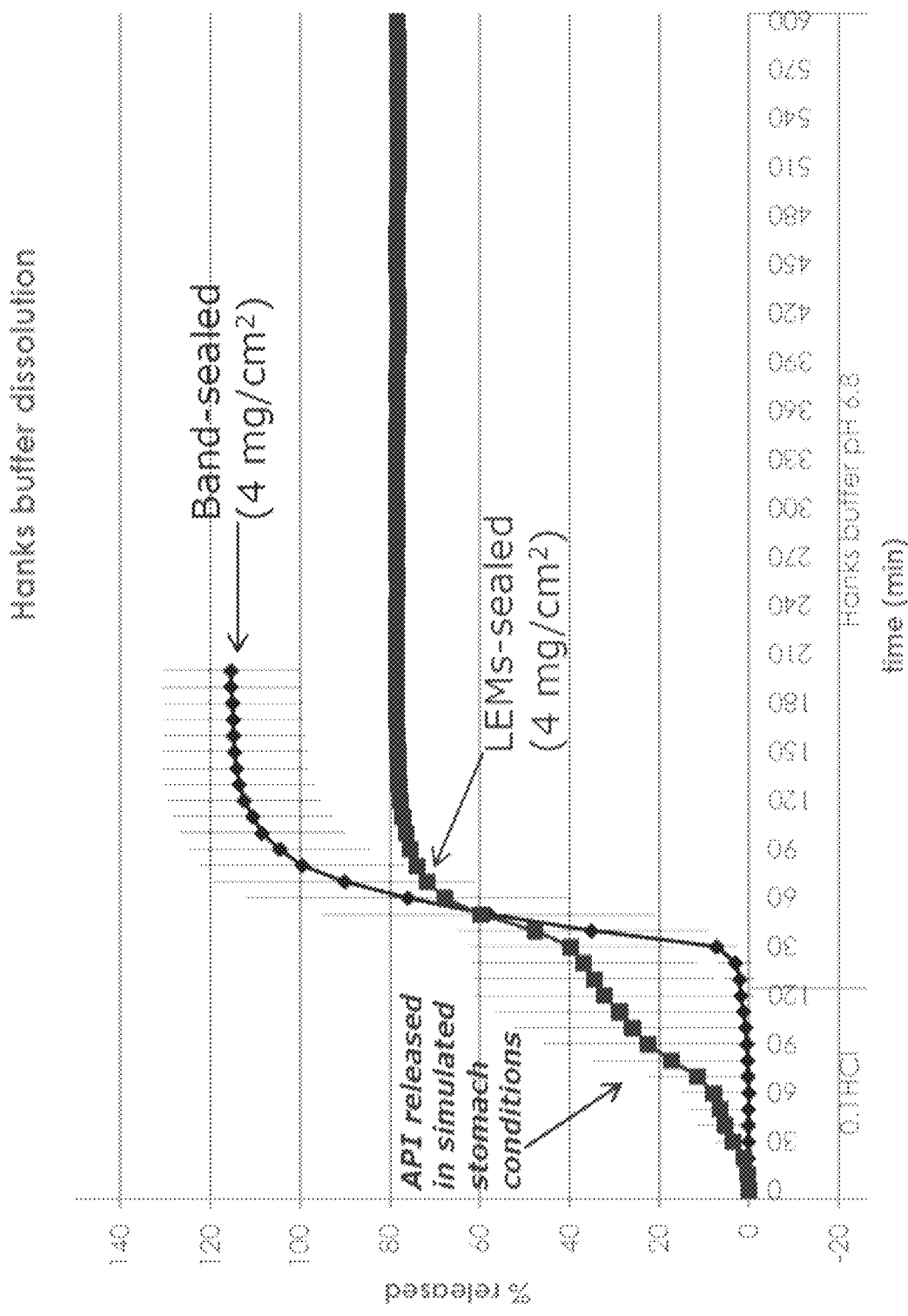
FIG. 11 shows dissolution profiles of capsules according to example 3 and of capsules according to comparative example 3.
Figure 12:
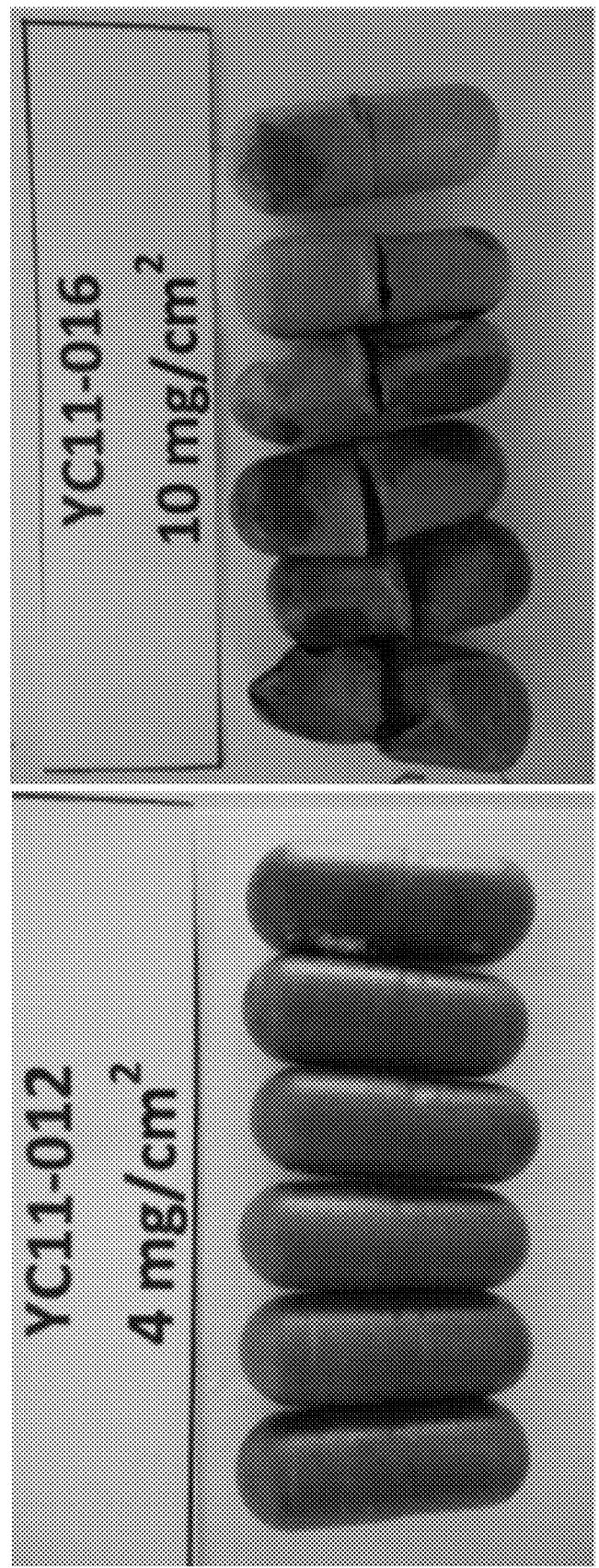
FIG. 12 shows capsules according to example 5 and capsules according to comparative example 5A after immersion into acid solution.
Figure 13:
FIG. 13 shows capsules according to comparative example 5B after immersion into acid solution.

Additionally, the release profiles of the capsules being coated with 4 mg/cm$^2$ of the film forming agent obtained in example 3 and comparative example 3 were measured. The results are shown in FIG. 11. While the capsules according to the invention show no significant release during immersion in 0.1 N HCl for 120 minutes and complete release after a lag time of about 37 minutes in Hanks buffer, the capsules of comparative example 3 being sealed with the LEMs technology instead of the sealing band showed significant release already during immersion in 0.1 N HCl.

Example 5

Size 1 hard HPMC capsules were filled with a model powder formulation containing methylene blue as marker. The capsules were closed and sealed with a HPMC band. Without any precoat, the capsules were then coated with an amount of 4 mg/cm$^2$ aqueous Eudragit L30D-55, relating to the dry amount of film forming agent per cm$^2$ of the final coating.

Comparative Example 5A

Capsules were manufactured in the same manner as in example 5 but without sealing the capsules with the HPMC band prior to the enteric coating.

Comparative Example 5B

Capsules were manufactured in the same manner as in comparative example 5A but with 3 mg/cm$^2$ HPMC precoat between the HPMC capsule shell and the Eudragit L30D-55 enteric coating.

Example 6

Size 1 hard gelatin capsules were filled with 314 mg of mesalazine (5-ASA). The capsules were closed and sealed with a gelatin band. Without any precoat, the capsules were then coated with aqueous Eudragit L30D-55 in an amount of 4 mg/cm$^2$ relating to the dry amount of film forming agent per cm$^2$ of the final coating. Then the capsules were coated with an additional coating comprising 60 mg of metronidazole benzoate.

Figure 14:
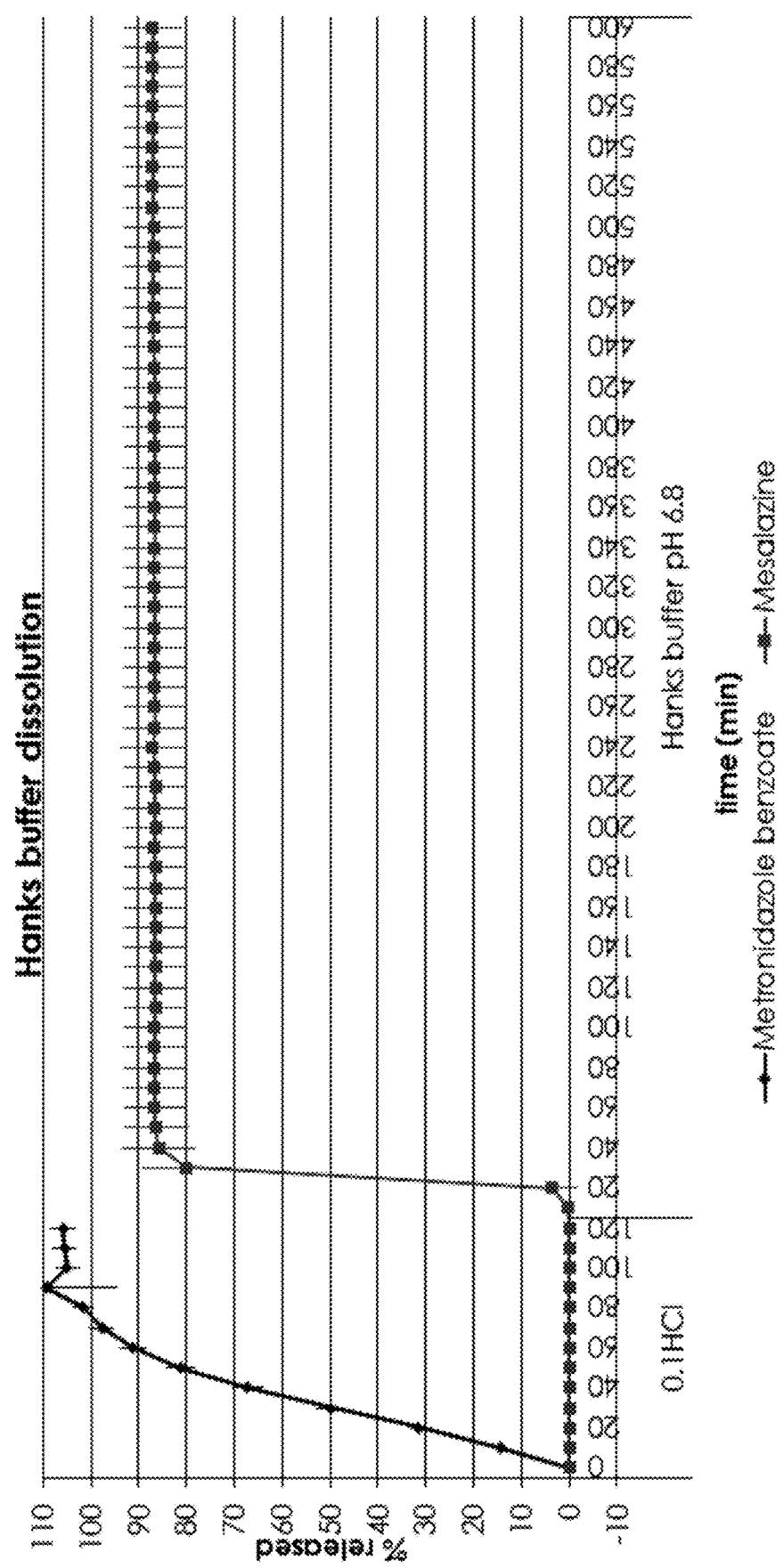
FIG. 14 shows a dissolution profile of a capsule according to example 6.

The release profiles of the capsules were measured using pH 6.8 Hanks buffer. In vitro dissolution studies were performed on a USP type II apparatus using a paddle speed of 50 rpm and a media temperature of 37±0.5° C. Capsules were first tested in 900 ml 0.1 N HCl for 2 hours followed by 8 or 10 hours in Hanks buffer (pH 6.8). The pH of the buffer was stabilized at 6.8±0.05 by continuously sparging with 5% $CO_2$/95% $O_2$. Metronidazole benzoate and mesalazine measurements were taken at 5 minute intervals. The composition per litre of Hanks buffer was 0.06 g of $KH_2PO_4$, 0.06 g $Na_2HPO_4.2H_2O$, 8.0 g NaCl, 0.4 g KCl, 0.2 g $MgSO_4.7H_2O$, 0.139 g $CaCl_2.2H_2O$ and 0.350 g $NaHCO_3$. The results are shown in FIG. 14.

Example 7

Size 1 hard gelatin capsules were filled with 312 mg of mesalazine (5-ASA). The capsules were closed and sealed with a gelatin band. Without any precoat, the capsules were then coated with a coating comprising metronidazole benzoate in Eudragit® RS in amounts of 20 mg (4 mg/cm$^2$ Eudragit® RS) and 60 mg (12 mg/cm$^2$ Eudragit® RS), respectively.

Comparative Example 7

Capsules were manufactured in the same manner as in example 7 but without sealing the capsules with the gelatin band prior to the coating.
Evaluation of Capsules According to Example 7 and Comparative Example 7

The release profiles of the capsules were measured using pH 6.8 Phosphate buffer. In vitro dissolution studies were performed on a USP type II apparatus using a paddle speed of 50 rpm and a media temperature of 37±0.5° C. Capsules were first tested in 900 ml 0.1 N HCl for 2 hours followed by 8 or 10 hours in Phosphate buffer (pH 6.8). Metronidazole benzoate and mesalazine measurements were taken at 5 minute intervals.

Figure 15:
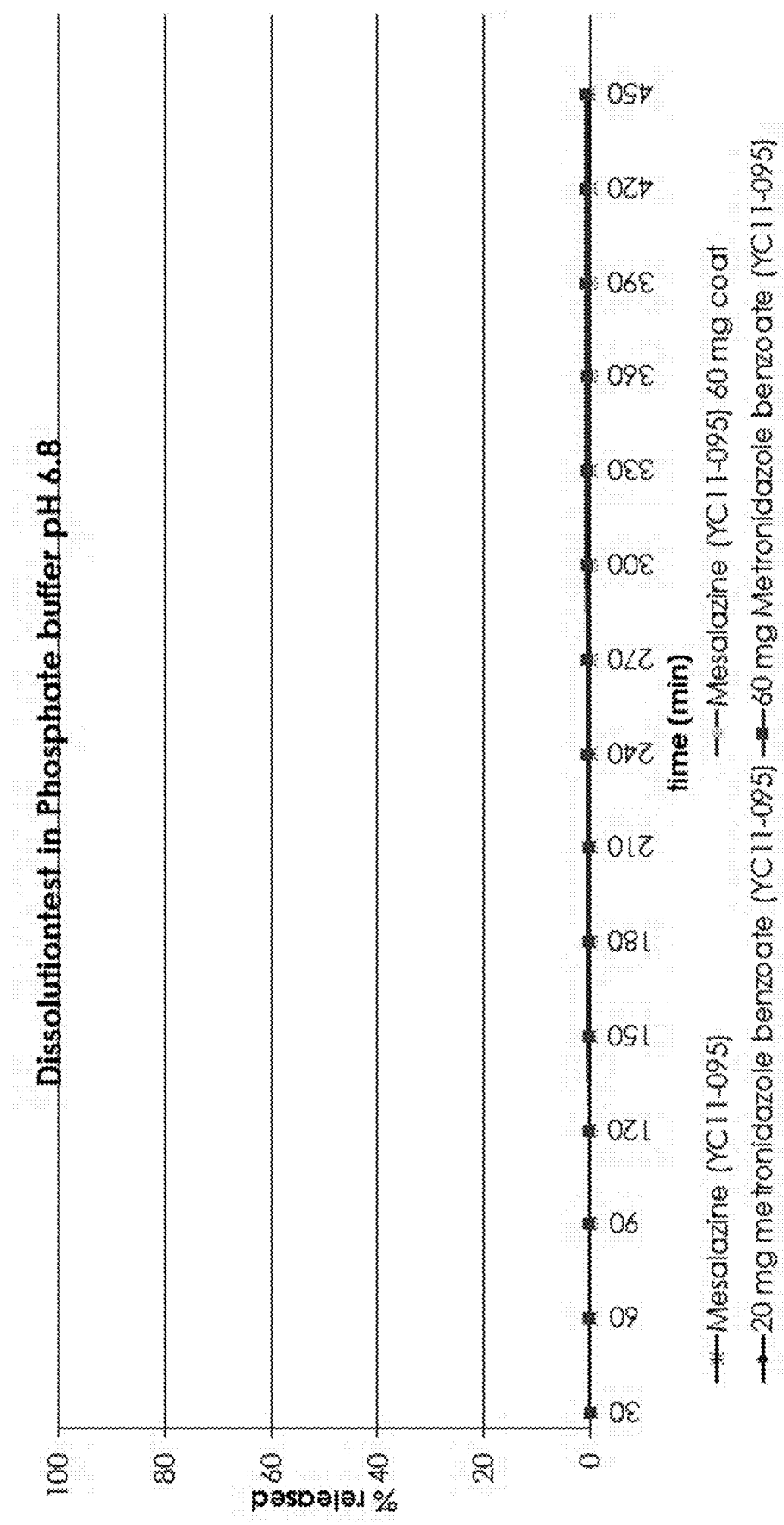
FIG. 15 shows dissolution profiles of capsules according to example 7.
Figure 16:
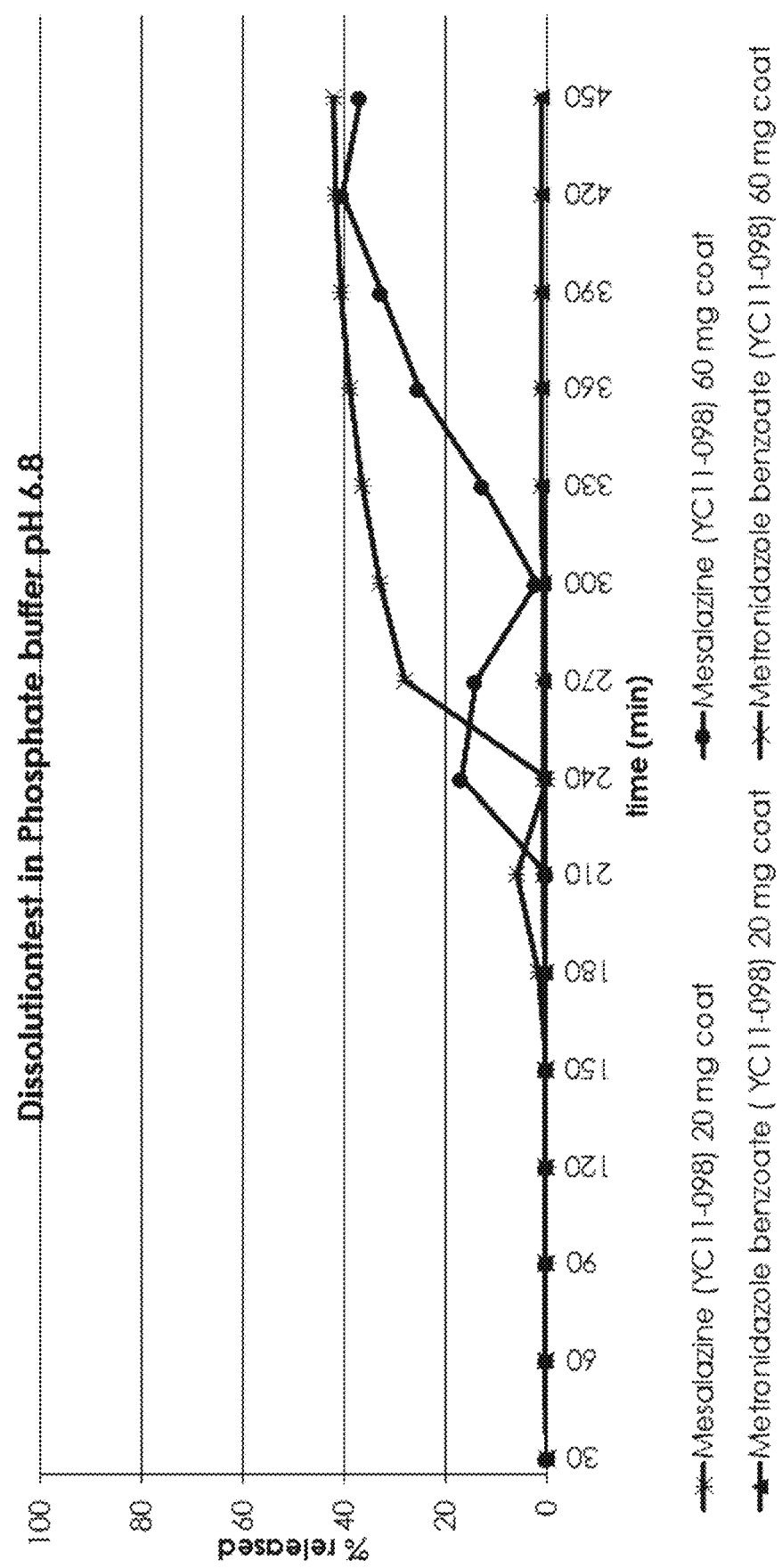
FIG. 16 shows dissolution profiles of capsules according to comparative example 7.

The release profiles of the capsules according to example 7 (banded capsules) and of the capsules of comparative example 7 (non-banded capsules) are shown in FIGS. 15 and 16. Both capsules were coated with 4 mg/cm$^2$ and 12 mg/cm$^2$ of the film forming agent, respectively.

The capsules according to the invention (example 7) did not release significant amounts of both, metronidazole benzoate and mesalazine under the simulated conditions of the intestine during a period of up to 450 minutes, irrespective of whether the capsules were coated with 4 mg/cm$^2$ or 12 mg/cm$^2$ of the film forming agent (FIG. 15). In contrast thereto, the non-banded capsules (comparative example 7) did release mesalazine under the simulated conditions of the intestine starting from 160 minutes (4 mg/cm$^2$) or 210 minutes (12 mg/cm$^2$), respectively. Metronidazole benzoate was not released under the above conditions (FIG. 16).

The invention claimed is:

1. A capsule filled with a liquid material comprising a body, a cap and a gap therebetween, characterized in that said capsule body and capsule cap define a capsule shell, wherein said capsule shell is a gelatin shell and said capsule further comprises a band seal and a modified release coating applied to said capsule shell, further wherein said band seal is a gelatin band sealing the gap between said capsule body and capsule cap, and said modified release coating is an enteric coating that includes a film forming agent in an amount of ≤8.0 mg/cm$^2$ of the modified release coating, further wherein there is no pre-coating between said capsule shell and said modified release coating, further wherein said enteric coating renders said capsule resistant against stomach acid while completely releasing its liquid material contents under intestinal tract conditions.

2. The capsule according to claim 1, wherein said film forming agent is selected from the group consisting of acrylate polymers, cellulose polymers, polyvinyl-based polymers and mixtures thereof.

3. The capsule according to claim 2, wherein said film forming agent is selected from the group consisting of co-polymers of (meth)acrylic acid and a (meth)acrylic acid $C_{1-4}$ alkyl ester, cellulose acetate phthalate, cellulose acetate trimellitate, cellulose acetate succinate, hydroxypropylmethyl cellulose phthalate, hydroxypropylmethyl cellulose acetate succinate, carboxymethylethyl cellulose acetate butyrate, polyvinyl acetate phthalate, and mixtures thereof.

4. The capsule according to claim 3, wherein said film forming agent is an anionic poly(methacrylic acid/methyl methacrylate) co-polymer having a pH threshold of 5.5, 6.0 or 7.

5. The capsule according to claim 1, wherein the film forming agent is present in an amount ranging from about 1 mg/cm$^2$ to 8.0 mg/cm$^2$ of the modified release coating.

6. The capsule according to claim 1, wherein the film forming agent is present in an amount ranging from about 2 mg to about 7 mg per cm$^2$ of the modified release coating.

7. The capsule according to claim 1, wherein the modified release coating additionally comprises at least one excipient selected from the group consisting of plasticizers, anti-tacking agents, colourants, pigments, solubilizers, dispersion agents and surfactants.

8. The capsule according to claim 1, wherein said liquid material comprises a nutritional ingredient and/or an active pharmaceutical ingredient.

9. The capsule according to claim 1, further comprising one or more additional coatings.

10. A process for manufacturing a liquid-filled capsule according to claim 1 comprised of a body, a cap and a gap therebetween, wherein said process comprises the steps of (i) filling the capsule body with said liquid material, (ii) closing the capsule with said cap, (iii) sealing the gap between body and cap with a gelatin band and (iv) applying a modified release coating onto the capsule shell, wherein the modified release coating is an enteric coting that includes a film forming agent in an amount of ≤8.0 mg/cm$^2$ of the modified release coating, further wherein there is no pre-coating between said capsule shell and said modified release coating, further wherein said enteric coating renders said capsule resistant against stomach acid while completely releasing its liquid material contents under intestinal tract conditions.

11. The process according to claim 10, wherein the modified release coating is applied onto the capsule shell in the form of an aqueous or non-aqueous liquid composition that includes the film forming agent.

12. A modified-release, liquid-filled, hard gelatin capsule comprising a capsule body and a capsule cap that together define a hard gelatin capsule shell filled with a liquid material, said capsule further comprising:
  (a) a gelatin band that seals a gap disposed between said capsule body and said capsule cap, and
  (b) a modified release enteric coating applied to said capsule shell;
wherein:
  (i) said capsule is free from any pre-coating disposed between said capsule shell and said modified release enteric coating,
  (ii) said liquid material comprises a nutritional ingredient and/or an active pharmaceutical ingredient,
  (iii) said modified release enteric coating comprises at least one excipient selected from the group consisting of anti-tacking agents, colourants, pigments, solubilizers, dispersion agents and surfactants, and further includes a film forming agent that is present in an amount ranging from about 3.5 mg/cm$^2$ to about 6.0 mg/cm$^2$ of the modified release enteric coating, and
  (iv) said enteric coating renders said capsule resistant against stomach acid while completely releasing its liquid material contents under intestinal tract conditions.

13. The capsule according to claim 12, wherein said film forming agent has a pH threshold of about 5.5 to about 7.0.

14. The capsule according to claim 12, wherein said modified release coating further comprises a polysaccharide colon targeting compound which is susceptible to attack by colonic bacteria, said compound selected from the group consisting of starch, amylose, amylopectine, chitosan, chondroitine sulfate, cyclodextrine, dextrane, pullulan, carrageenan, scleroglucan, chitin, curdulan, pectin, guar gum, xanthan gum and levan.

* * * * *